US005468849A

United States Patent [19]
Lam et al.

[11] Patent Number: 5,468,849
[45] Date of Patent: Nov. 21, 1995

[54] REBECCAMYCIN ANALOGS BY TRYPTOPHAN ANALOGS FEEDING

[75] Inventors: Kin S. Lam, Cheshire; Daniel R. Schroeder, Higganum; Jacqueline Mattei, Branford; Salvatore Forenza; James A. Matson, both of Cheshire, all of Conn.

[73] Assignee: Bristol-Myers Squibb Company, New York, N.Y.

[21] Appl. No.: 216,075

[22] Filed: Mar. 21, 1994

Related U.S. Application Data

[63] Continuation of Ser. No. 60,951, May 13, 1993, abandoned, which is a continuation of Ser. No. 648,751, Feb. 5, 1991, abandoned, which is a continuation-in-part of Ser. No. 489,430, Mar. 6, 1990, abandoned.

[51] Int. Cl.$^6$ .......................... C07G 3/00; C07H 11/00; C07H 17/02; C12P 19/28
[52] U.S. Cl. .................. 536/18.5; 536/18.7; 536/16.8; 536/16.9; 536/22.1; 435/85; 435/87
[58] Field of Search ...................... 514/42, 43; 536/22.1, 536/16.9, 16.8, 18.5, 18.7; 435/85, 87

[56] References Cited

U.S. PATENT DOCUMENTS

| | | | |
|---|---|---|---|
| 4,487,925 | 12/1984 | Nettleton et al. | 536/24 |
| 4,552,842 | 11/1985 | Nettleton et al. | 435/75 |
| 4,785,085 | 11/1988 | Kaneko et al. | 536/26 |
| 4,808,613 | 2/1989 | Kaneko et al. | 514/42 |

OTHER PUBLICATIONS

Pazoutova, S., et al., "The Inhibition of Clavine Biosynthesis by 5-Fluorotryptophan; a Useful Tool for the Study of Regulatory and Biosynthetic Relationships in Claviceps," Applied Microbiology and Biotechnology, 33:330–334 (1990).
Adams, E. S., et al., "Directed Biosynthesis of 5"-Fluoropactamycin in *Streptomyces pactum*," The Journal of Antibiotics, 47:(12), pp. 1456–1465 (1994).
Cannell, R. J. P., et al., "Production of Additional Squalestatin Analogues by Directed Biosynthesis," The Journal of Antibiotics, 47:(2), pp. 247–249 (1994).
Cannell, R. J. P., et al., "The Squalestatins, Novel Inhibitors of Squalene Synthase Produced by a Species of Phoma," The Journal of Antibiotics, 46:(9), pp. 1381–1389 (1993).
Chen, T. S., et al., "The Preparation of Zaragozic Acid A Analogues by Directed Biosynthesis," The Journal of Antibiotics, 47:(11), pp. 1290–1294 (1994).
Becker, A. M., et al., "3–Amino–5–Hydroxybenzoic Acid in Antibiotic Biosynthesis VI. Directed Biosynthesis Studies with Ansamycin Antibiotics", The Journal of Antibiotics, 36:(10), pp. 1323–1327 (1983).
Lam, K. S., et al., "Isolation of a Bromo Analog of Rebeccamycin From *Saccharothrix aerocolonigenes*," The Journal of Antibiotics, 44:(9), pp. 934–939 (1991).
"Isosterism and Molecular Modification in Drug Design," Chemical Society Reviews, vol. 8, pp. 563–579 (1979).
Houck, D. R., et al., "On the Biosynthesis of Asperlicin and the Directed Biosynthesis of Analogs in *Aspergillus Alliaceus*," The Journal of Antibiotics, 41:(7), pp. 882–891 (1988).
Bush, J. A. et. al., J. Antibiotics, 40:668–678 (1987).

*Primary Examiner*—David T. Fox
*Assistant Examiner*—Howard C. Lee
*Attorney, Agent, or Firm*—Michelle A. Kaye; Samuel J. DuBoff

[57] ABSTRACT

Addition of certain tryptophan analogs to the culture medium during fermentation of a rebeccamycin-producing strain of *Saccharothrix aerocolonigenes* results in production of new rebeccamycin analogs having advantageous antitumor properties.

6 Claims, 15 Drawing Sheets

5,468,849

REBECCAMYCIN ANALOGS BY TRYPTOPHAN ANALOGS FEEDING

This application is a continuation of application Ser. No. 08/060,951, filed May 13, 1993, now abandoned, which is a continuation of application Ser. No. 07/648,751, filed Feb. 5, 1991, now abandoned, which is a CIP of application Ser. No. 07/489,430 filed Mar. 6, 1990, now abandoned.

BACKGROUND OF THE INVENTION

1. Field of the Invention

This invention relates to novel analogs of rebeccamycin which posses antineoplastic properties.

2. Background Art

U.S. Pat. Nos. 4,487,925 and 4,552,842 disclose the anti-tumor agent designated rebeccamycin, and the 5'-methyl and 5',2',3",6"-tetraacetate derivatives thereof, and a process for producing the same agent by cultivating a rebeccamycin-producing strain of *Nocardia aerocolonigenes*, preferably *Nocardia aerocolonigenes* ATCC 39243, or a rebeccamycin-producing mutant thereof in an aqueous nutrient medium containing assimilable sources of carbon and nitrogen under submerged aerobic conditions until a substantial amount of rebeccamycin is produced. Recently, *Nocardia aerocolonigenes*, ATCC 39243 was reclassified as *Saccharothrix aerocolonigenes*, ATCC 39243 (Bush et at, *J. Antibiotics*, 40:668–678, 1987).

SUMMARY OF THE INVENTION

The present invention provides new analogs of the anti-tumor agent designated rebeccamycin (Formula I).

Formula I

More specifically, there are provided rebeccamycin analogs of the Formulas II and III below, Formula II Formula III wherein $X_1$ and $X_2$ are independently fluorine or hydrogen, provided that $X_1$ and $X_2$ are not simultaneously hydrogen; as well as pharmaceutically acceptable acid addition salts of such analogs.

The compounds of the Formulas II and III are produced by supplementing the cultures of a rebeccamycin producing strain of *Saccharothrix aerocolonigenes* with the appropriate tryptophan analog.

DETAILED DESCRIPTION OF THE INVENTION

Figure 1:
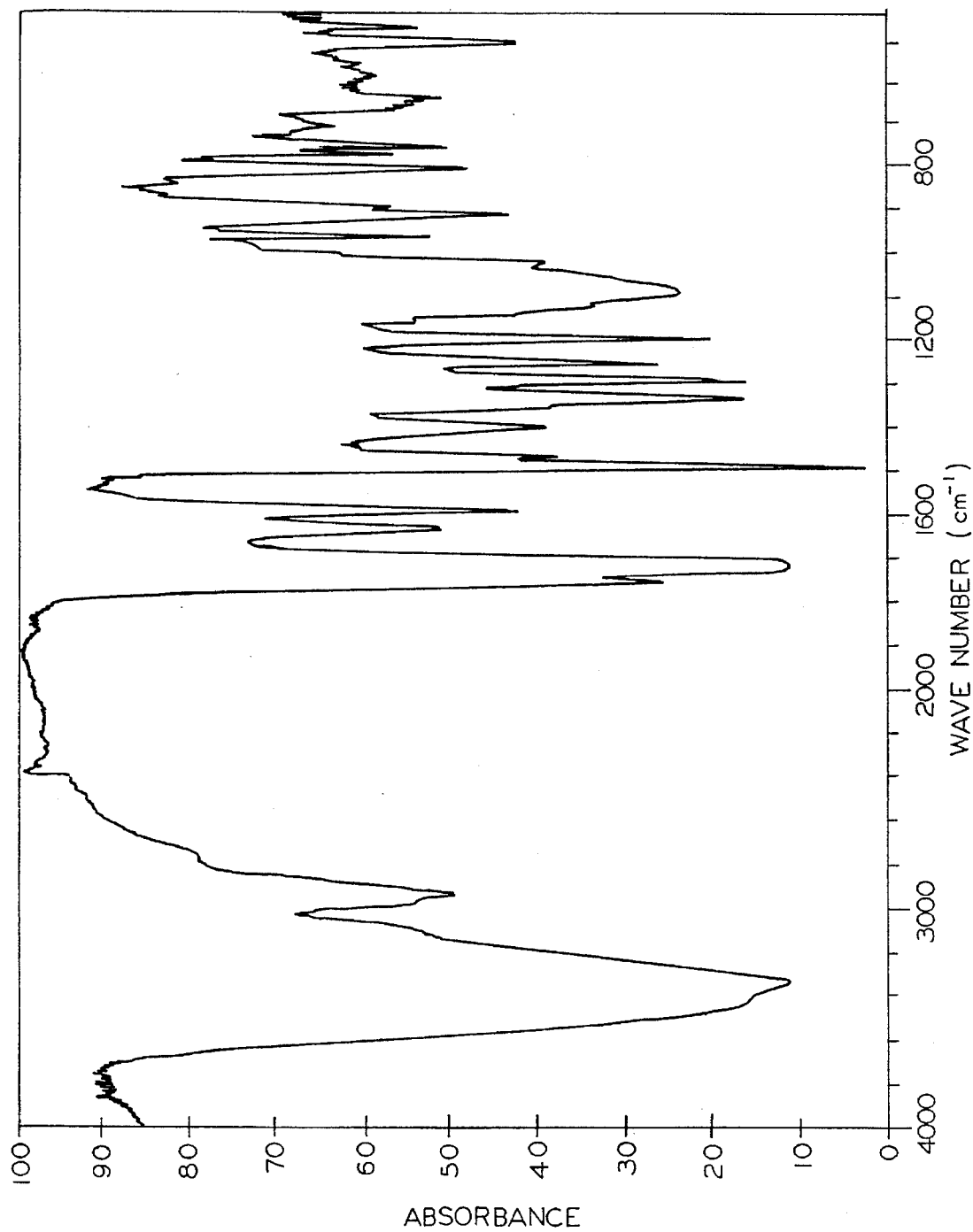
FIG. 1 shows the IR spectrum for the compound of Formula IV.
Figure 2:
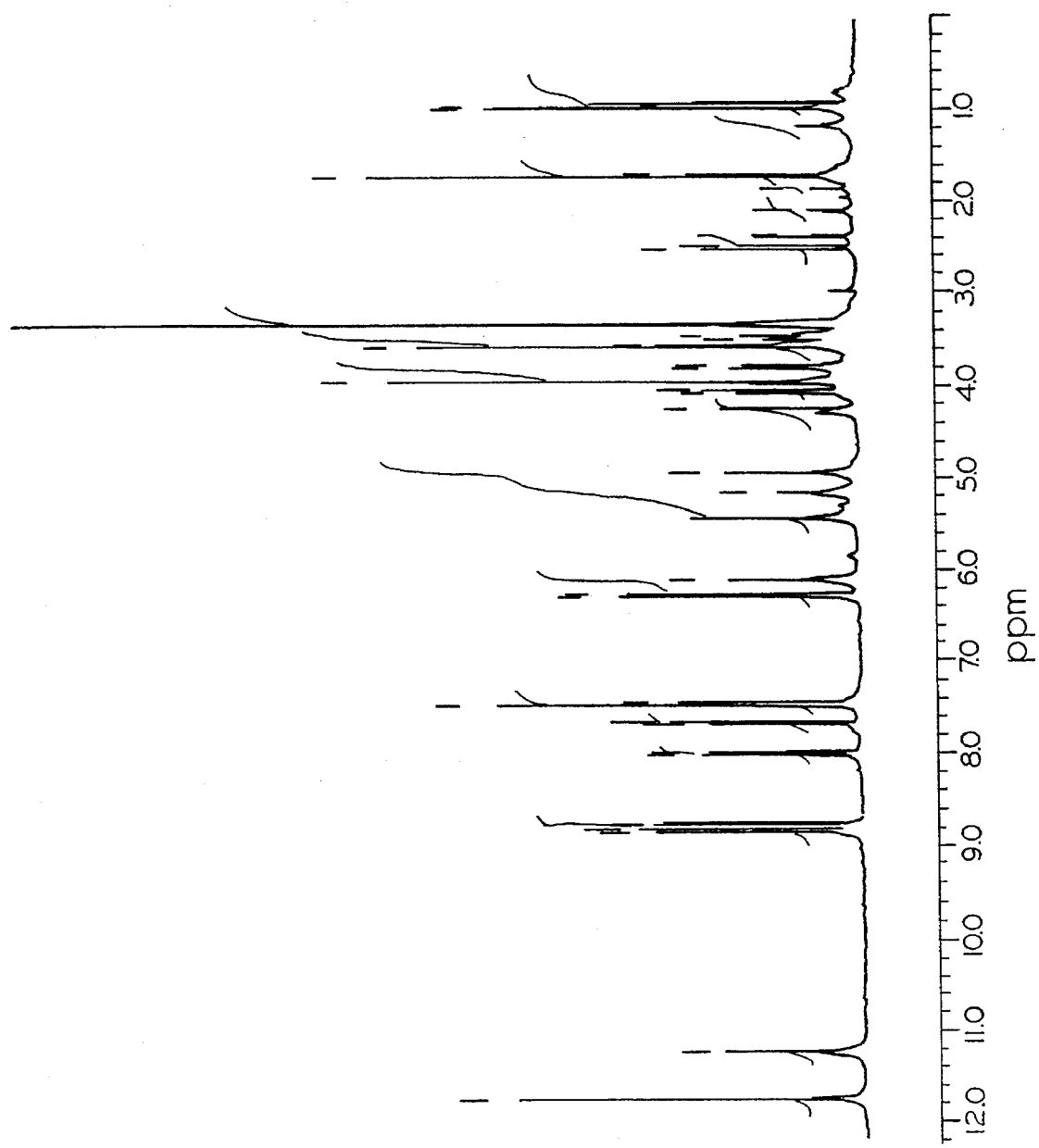
FIG. 2 shows the $^1$H-NMR for the compound of Formula IV.
Figure 3:
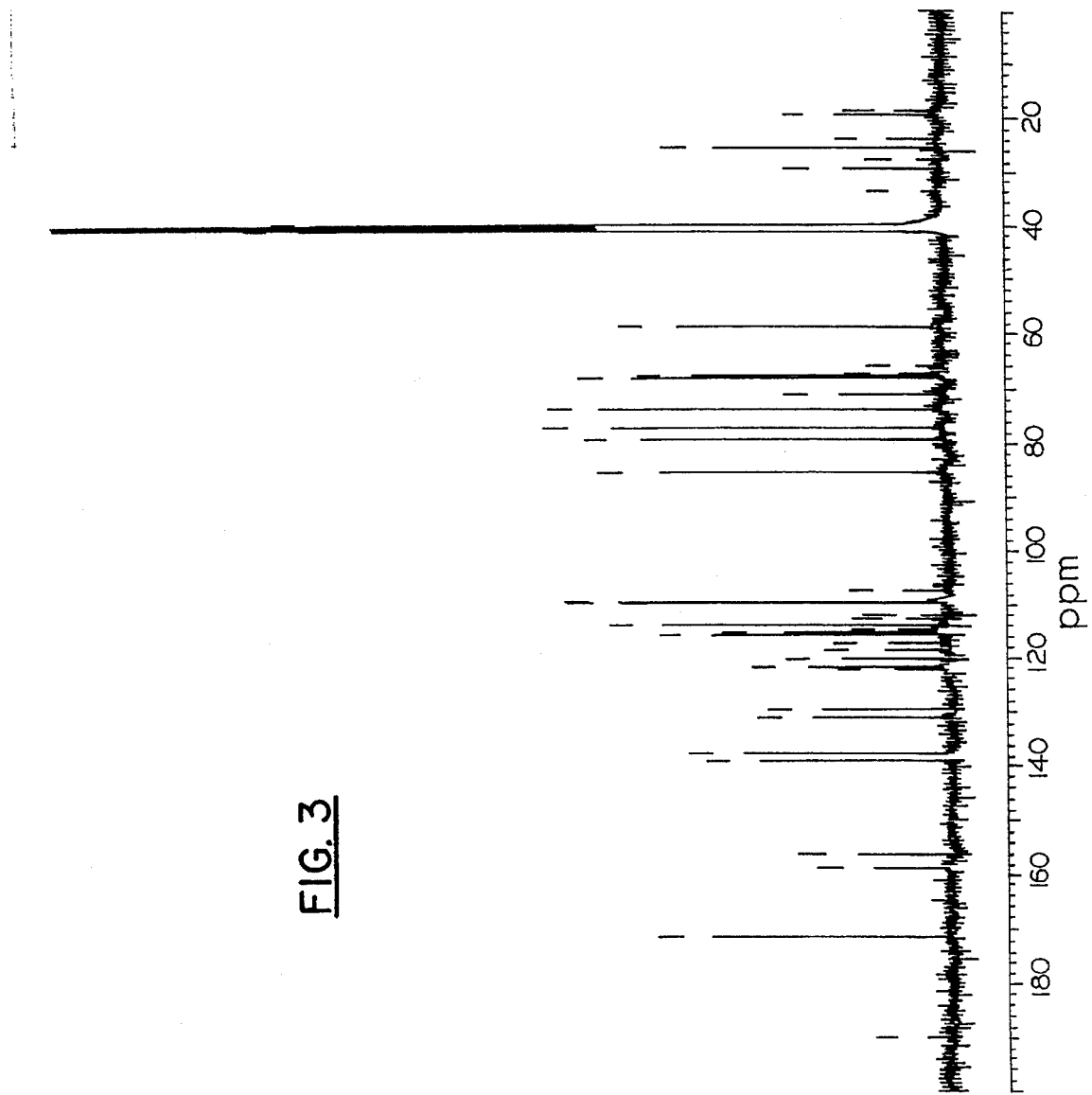
FIG. 3 shows the $^{13}$C-NMR for the compound of Formula IV.
Figure 4:
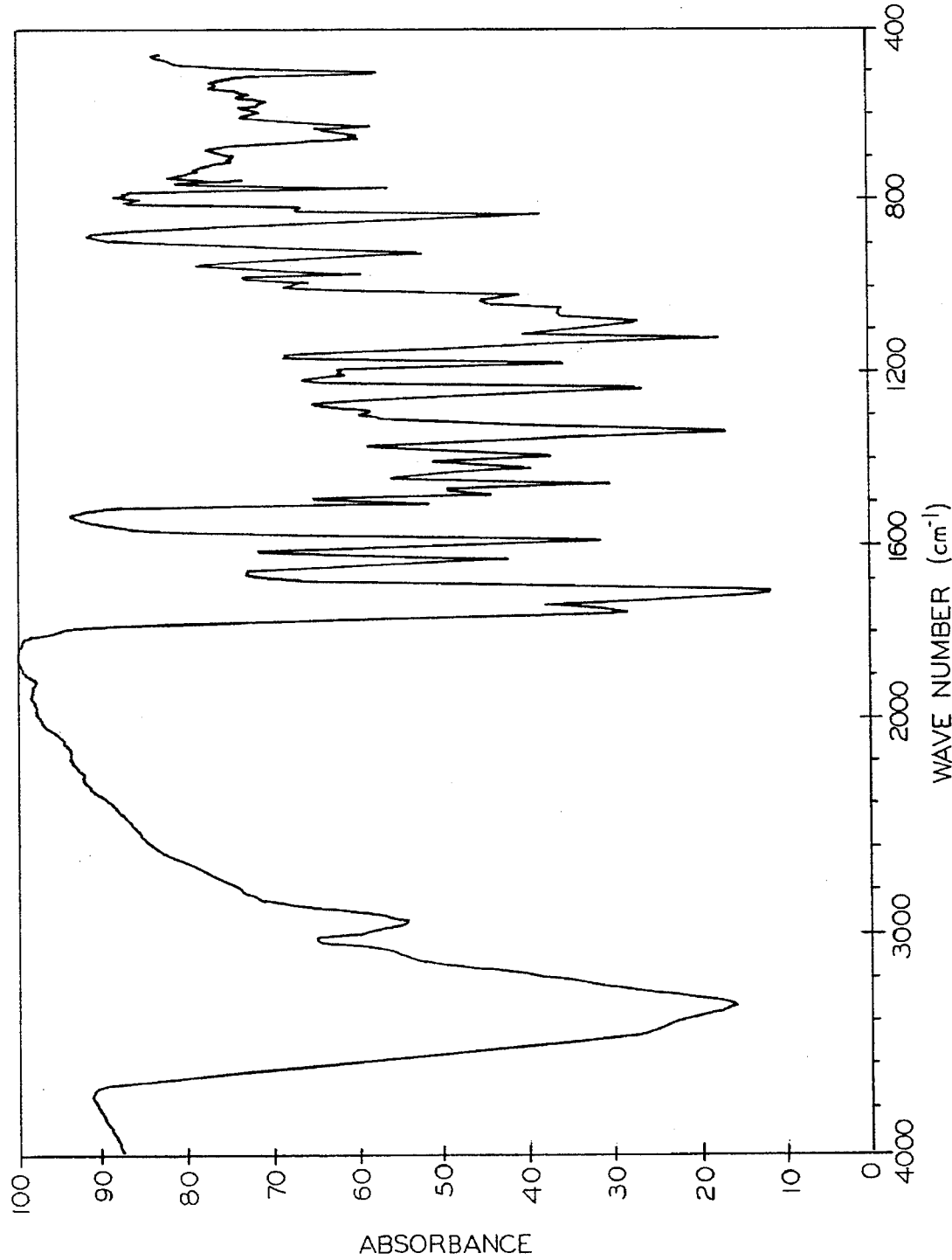
FIG. 4 shows the IR spectrum for the compound of Formula V.
Figure 5:
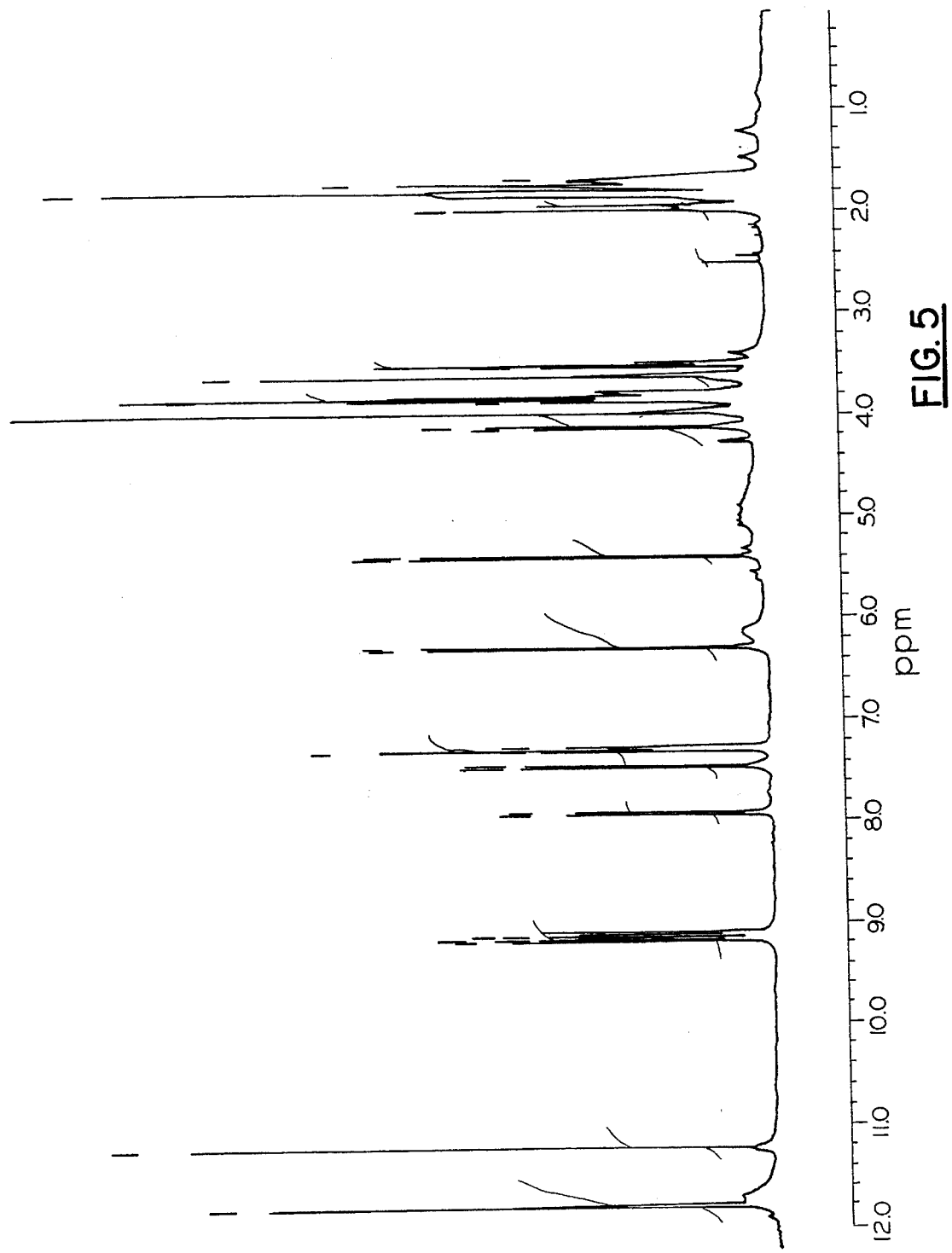
FIG. 5 shows the $^1$H-NMR for the compound of Formula V.
Figure 6:
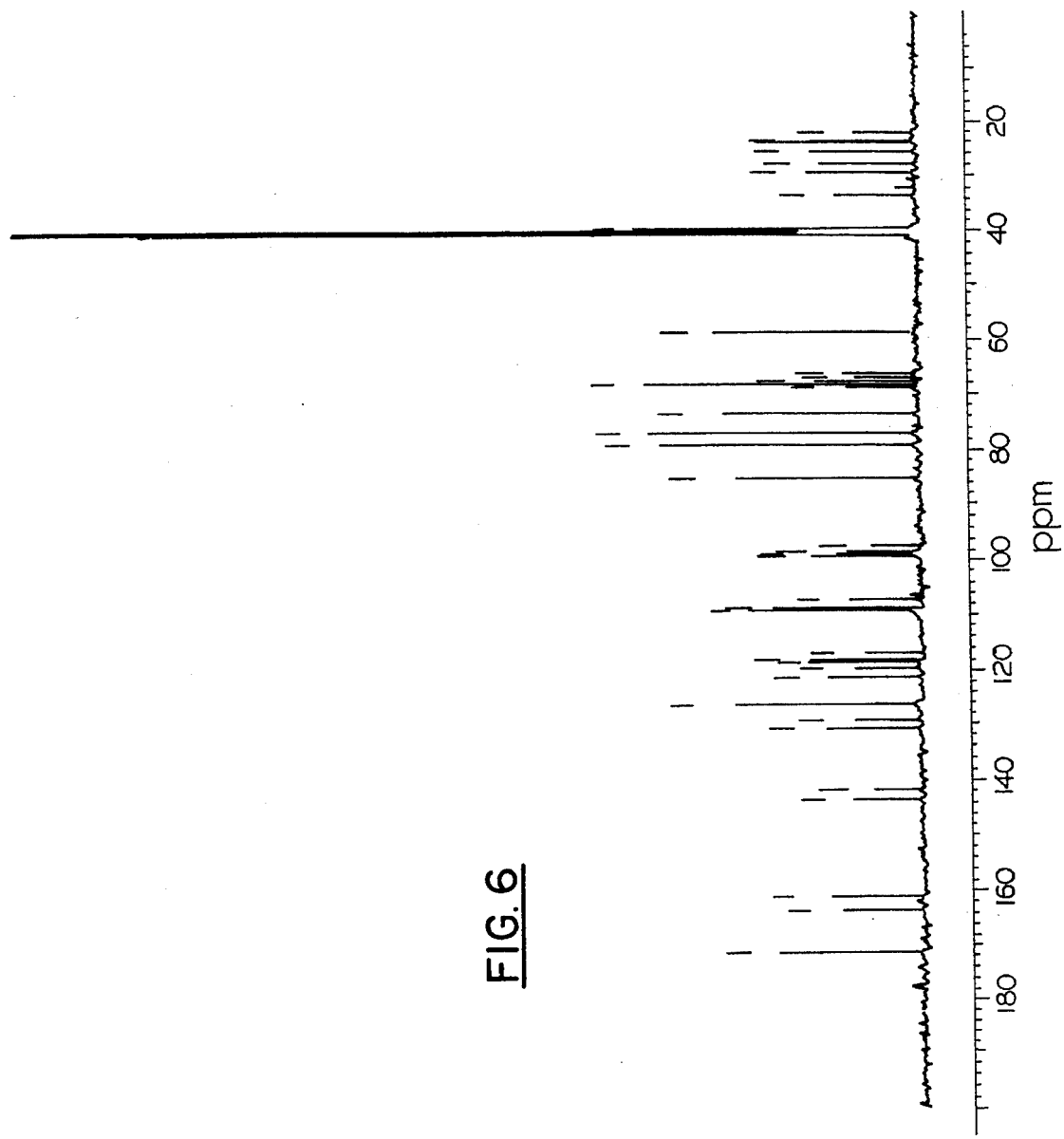
FIG. 6 shows the $^{13}$C-NMR for the compound of Formula V.
Figure 7:
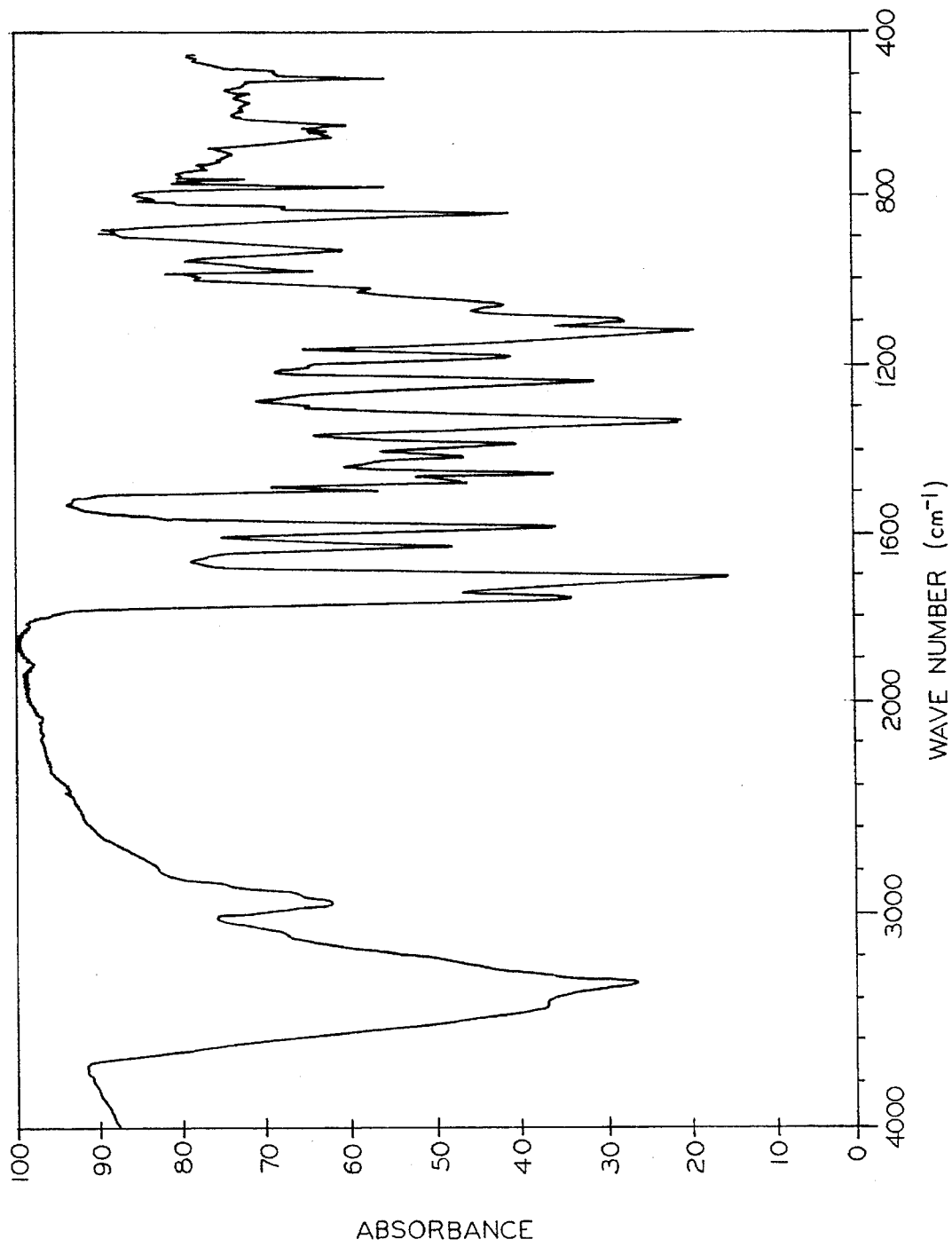
FIG. 7 shows the IR spectrum for the compound of Formula VIII.
Figure 8:
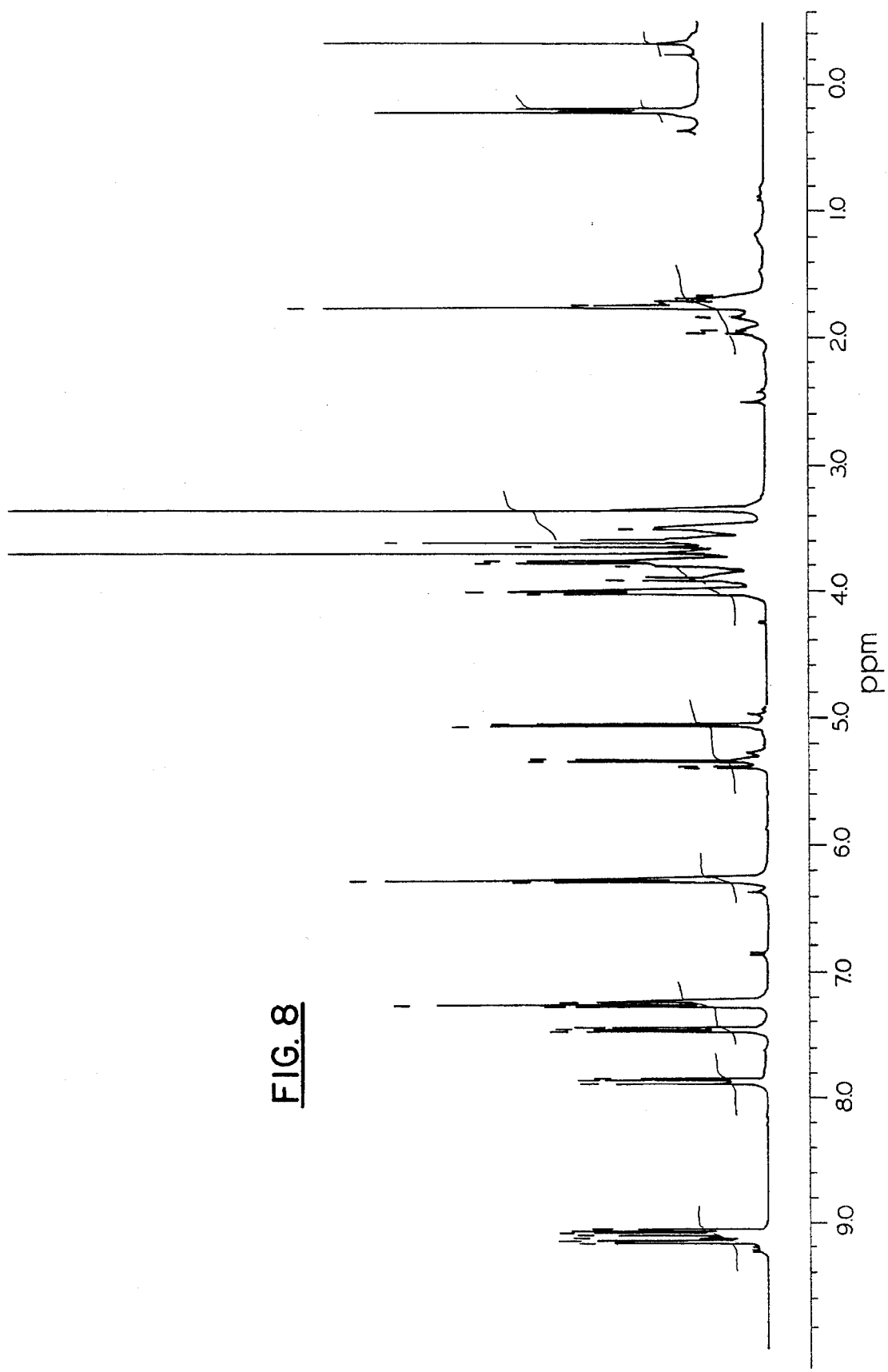
FIG. 8 shows the $^1$H-NMR for the compound of Formula VIII.
Figure 9:
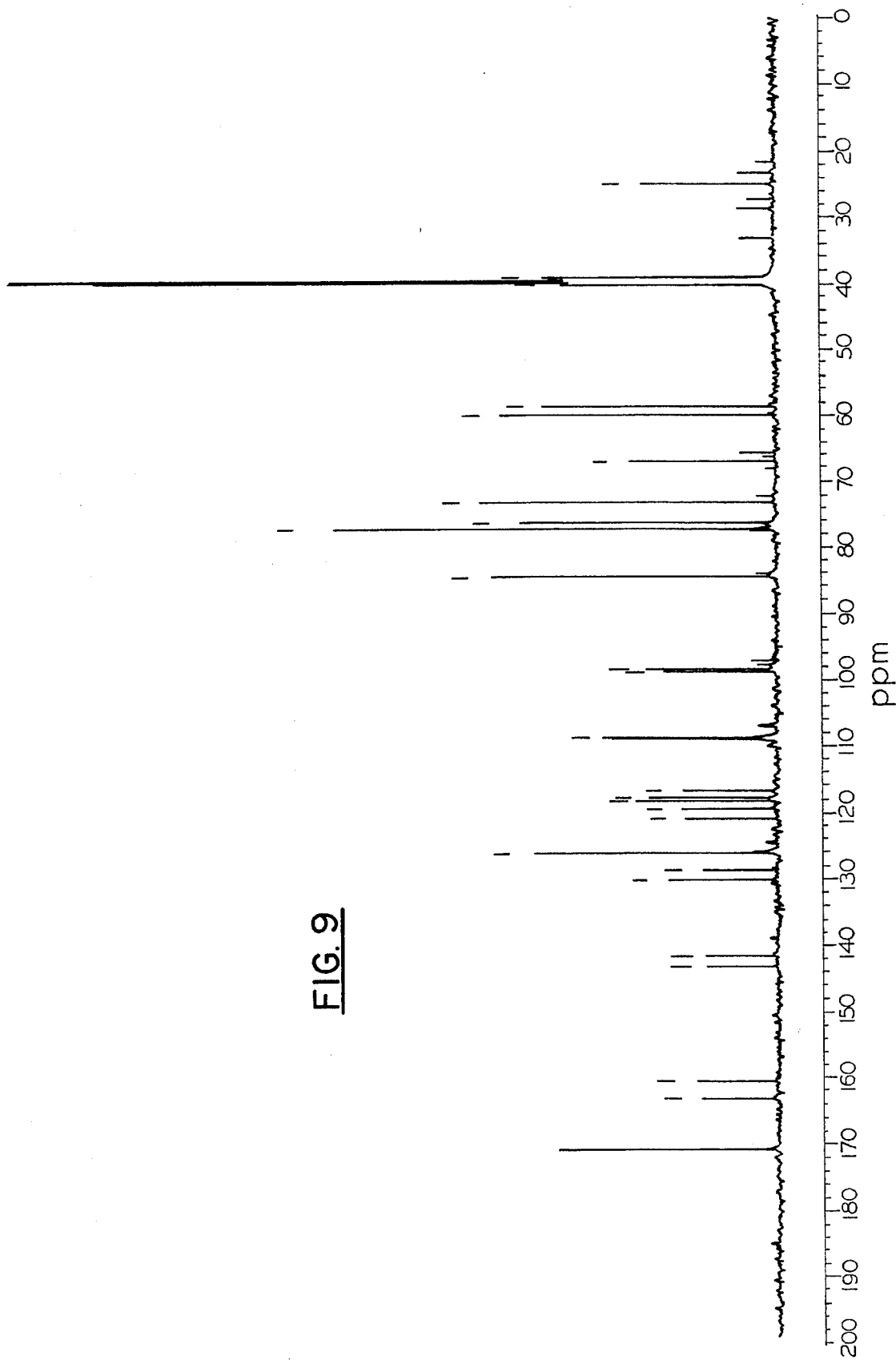
FIG. 9 shows the $^{13}$C-NMR for the compound of Formula VIII.
Figure 10:
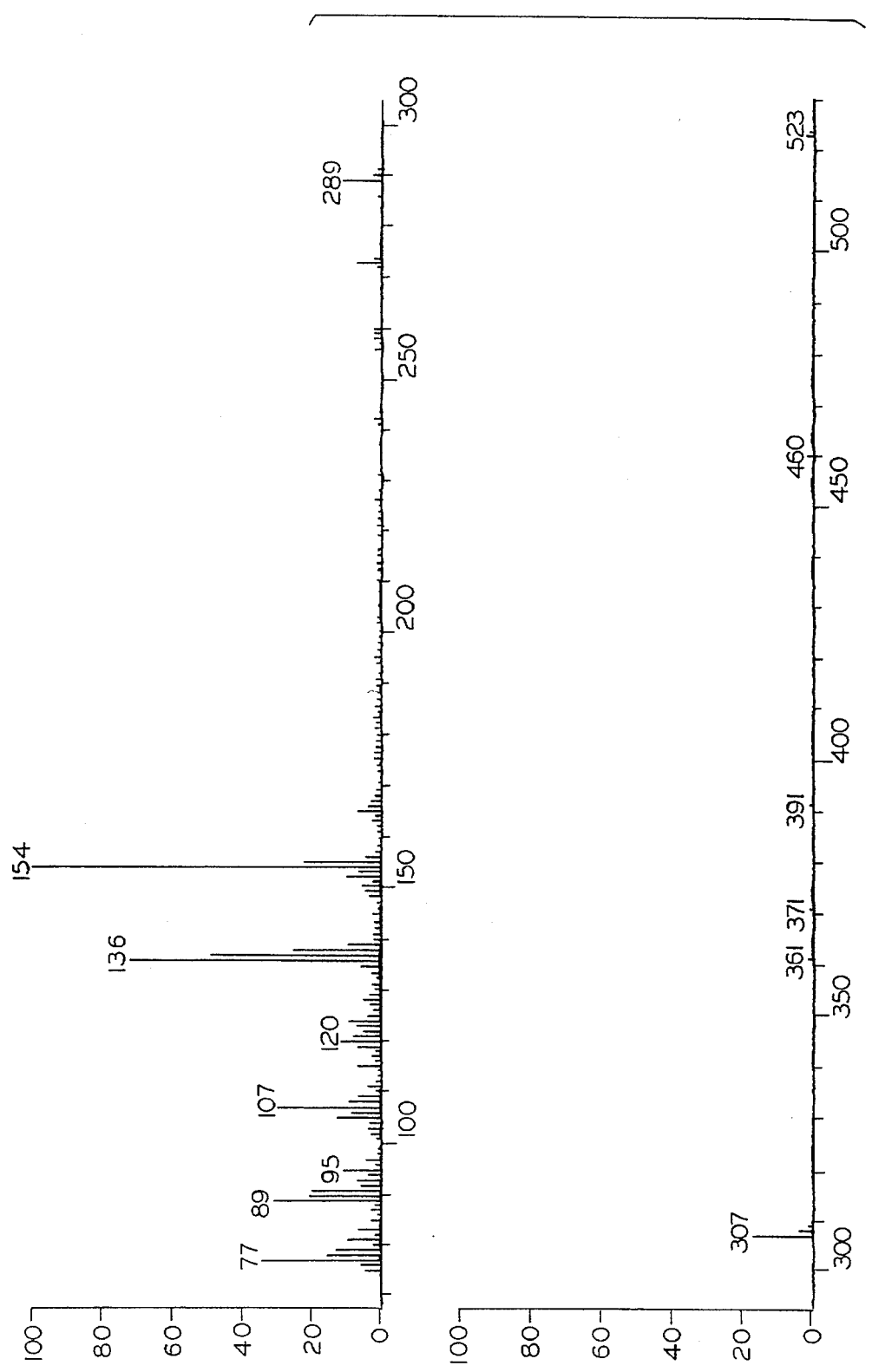
FIG. 10 shows the mass spectrum of the compound of Formula IV.
Figure 11:
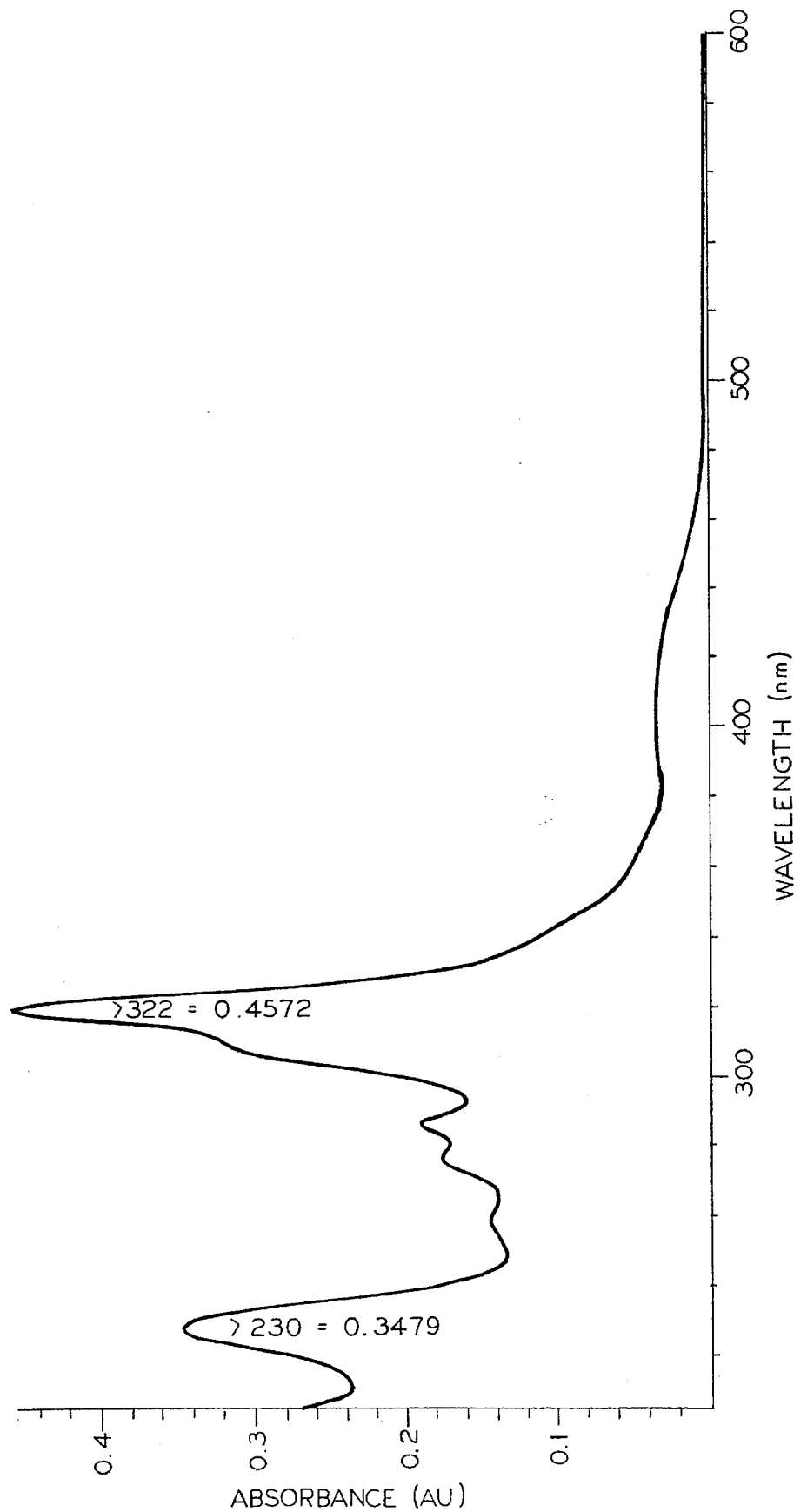
FIG. 11 shows the UV spectrum of the compound of Formula IV.
Figure 12:
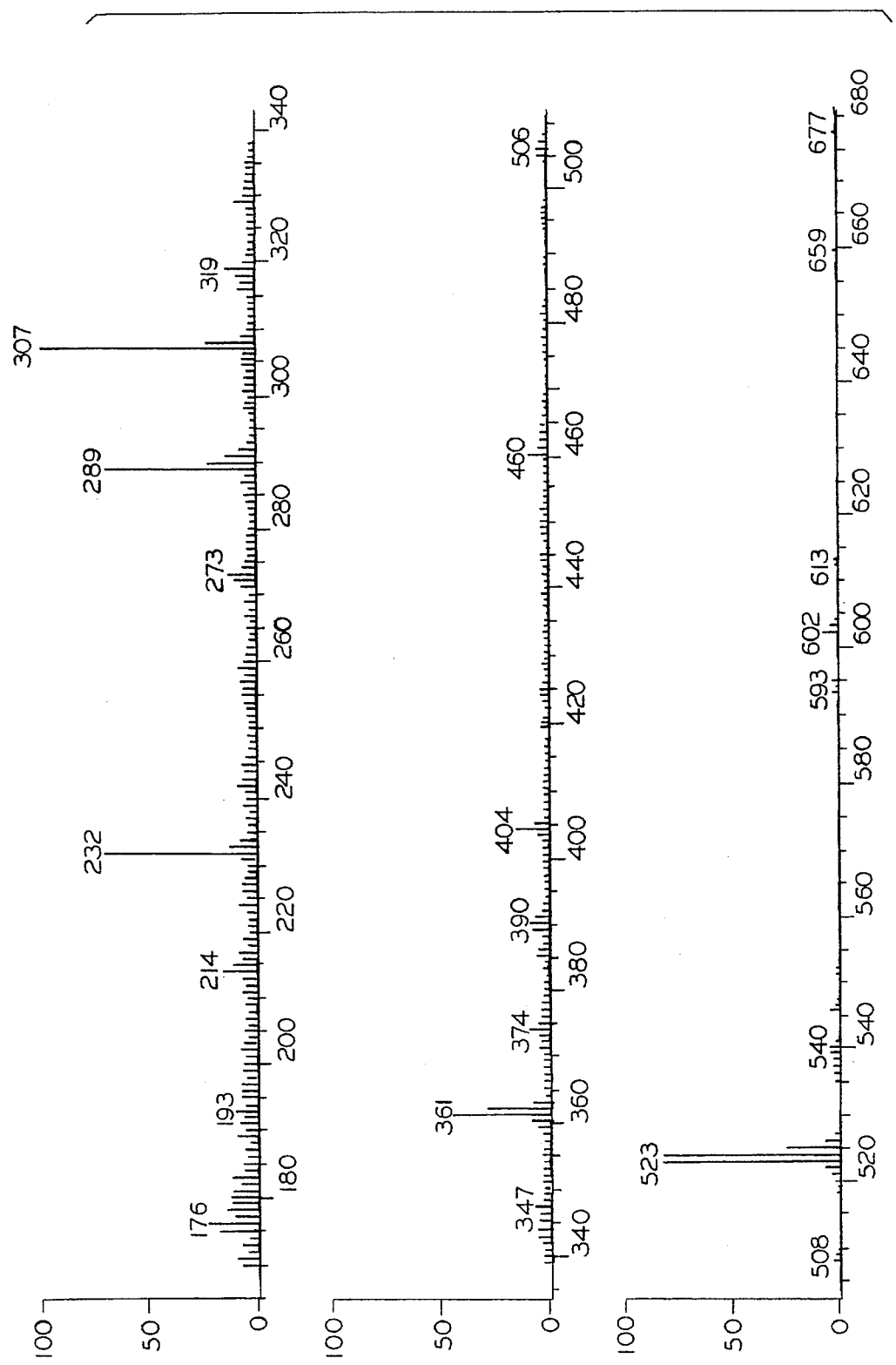
FIG. 12 shows the mass spectrum of the compound of Formula V.
Figure 13:
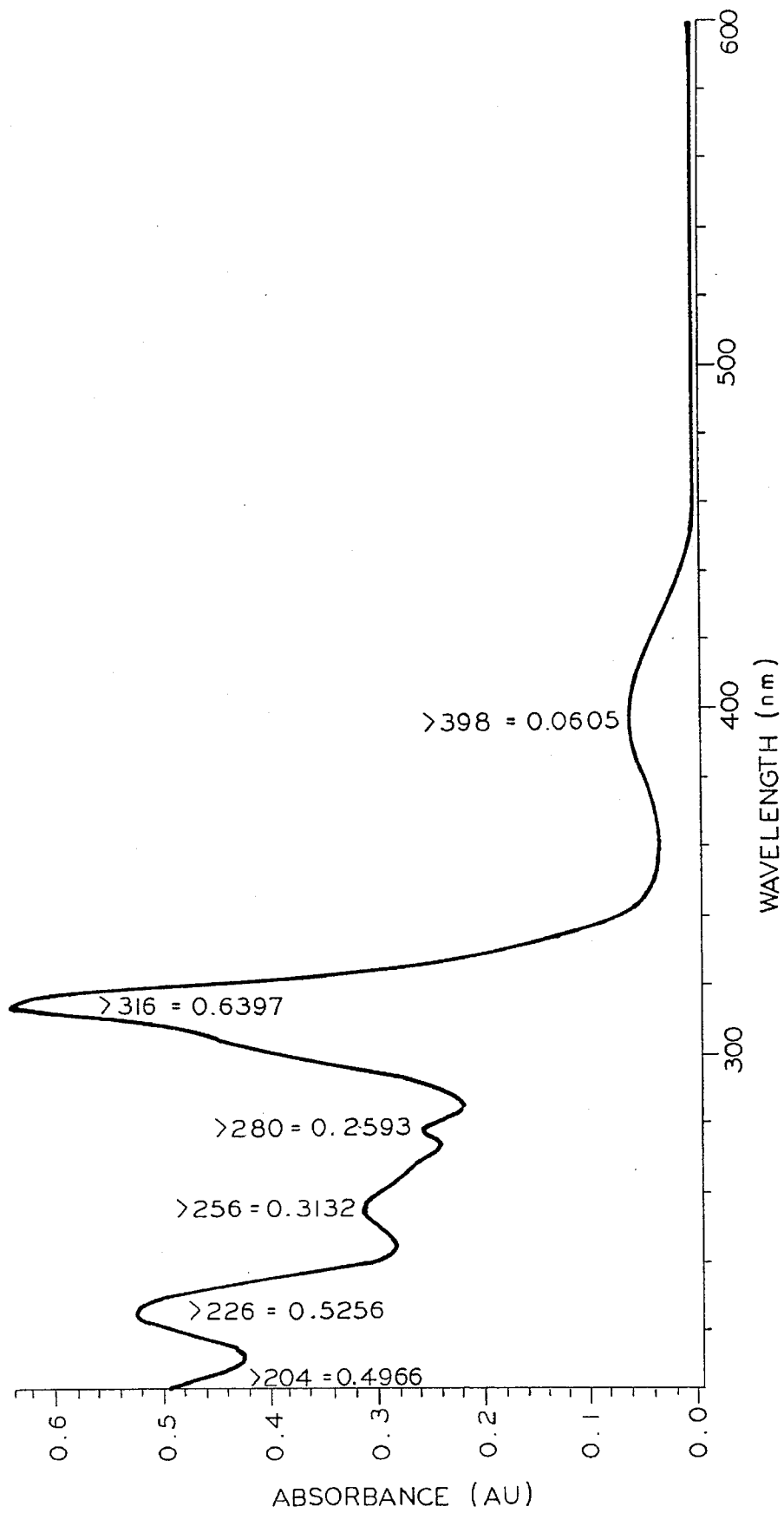
FIG. 13 shows the UV spectrum of the compound of Formula V.
Figure 14:
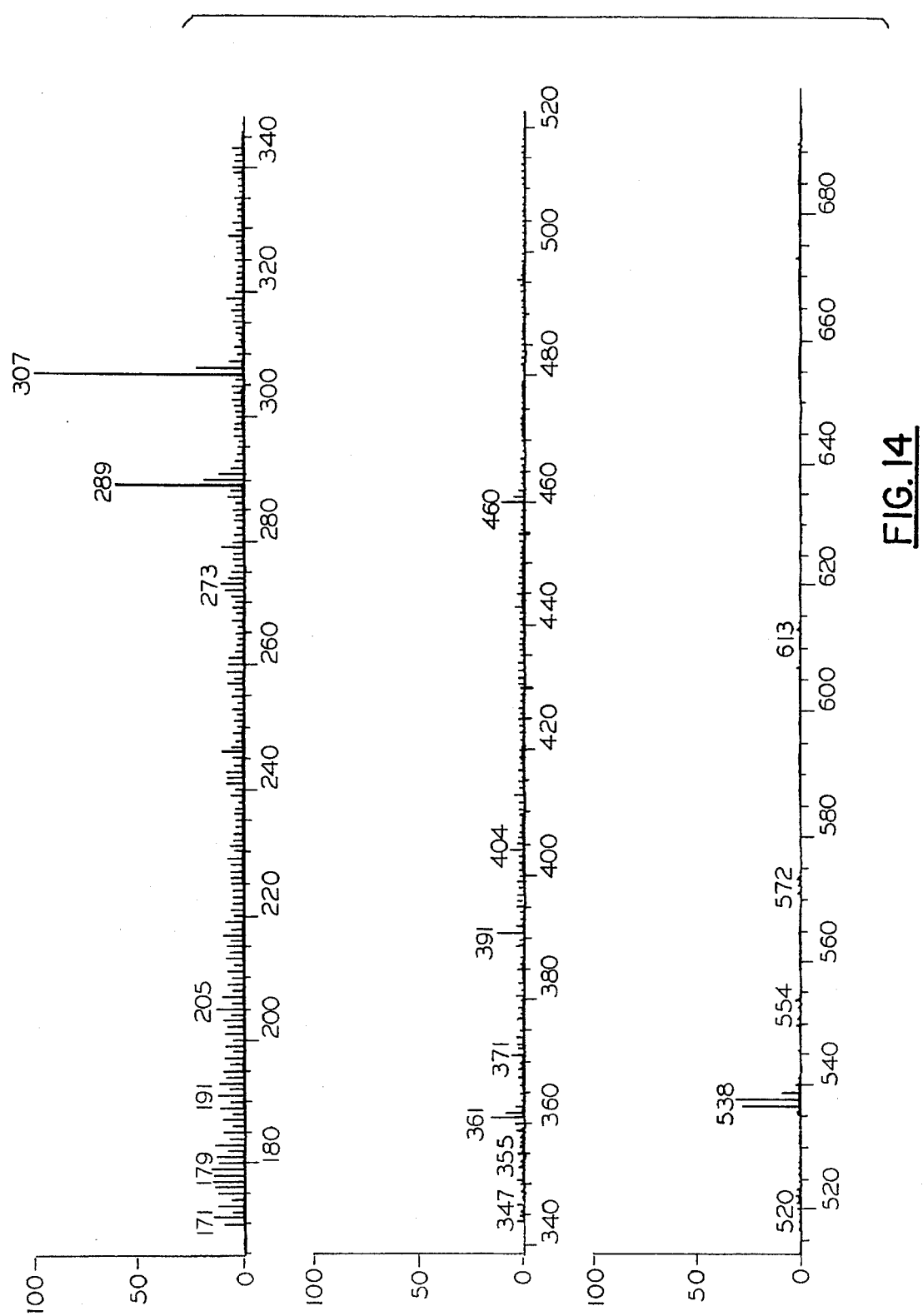
FIG. 14 shows the mass spectrum of the compound of Formula VIII.
Figure 15:
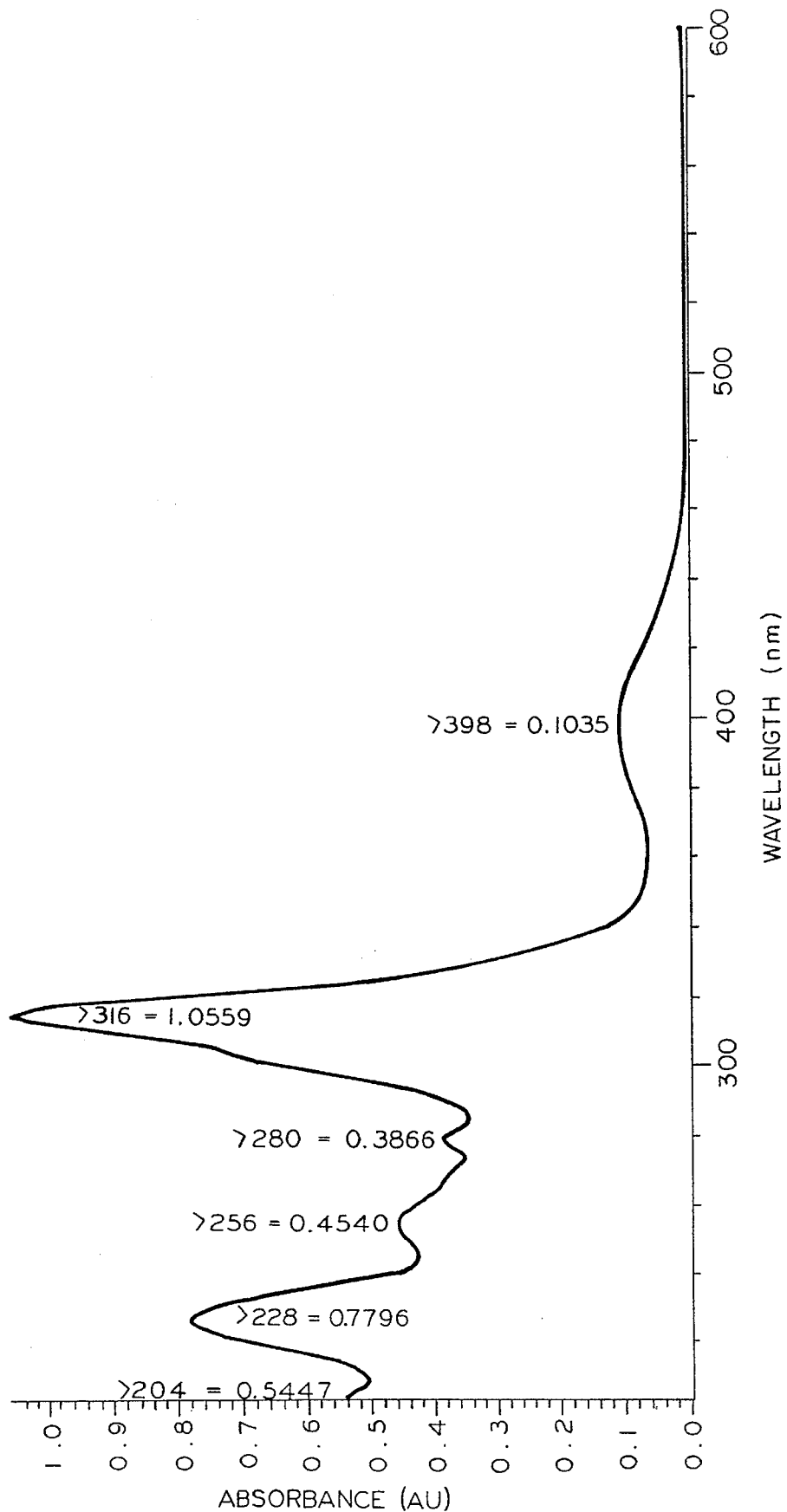
FIG. 15 shows the UV spectrum of the compound of Formula VIII.

U.S. Pat. Nos. 4,487,925 and 4,552,842 disclose the production and isolation of the antitumor agent designated rebeccamycin (Formula I)

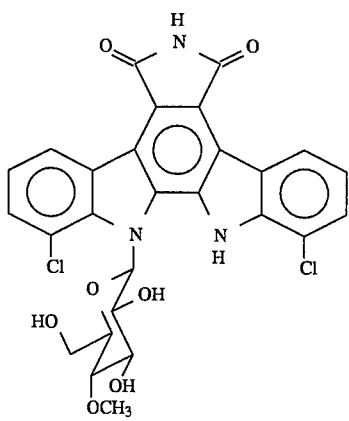

Formula I

The above-mentioned rebeccamycin compound is the principal component of the fermentation of the rebeccamycin producing strain of *Saccharothrix aerocolonigenes*.

It has now been found according to the present invention that the fermentation procedure disclosed in U.S. Pat. Nos. 4,487,925 and 4,552,842 can be carried out in the presence of certain tryptophan analogs to produce new analogs of rebeccamycin having valuable antitumor properties. The rebeccamycin analogs of the present invention have the Formulas II and III below.

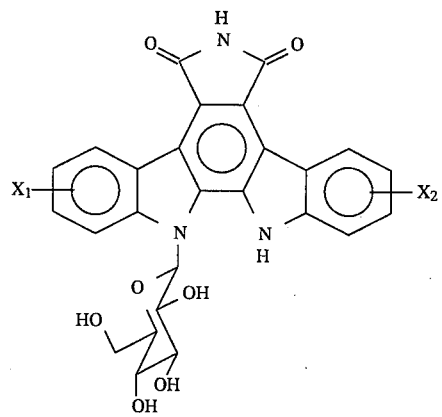

Formula II

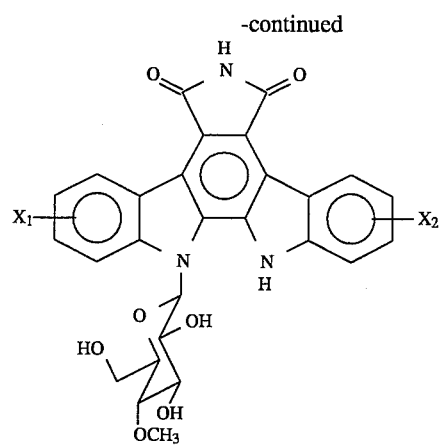

Formula III wherein $X_1$ and $X_2$ are fluorine or hydrogen, provided that $X_1$ and $X_2$ are not simultaneously hydrogen; as well as pharmaceutically acceptable acid addition salts thereof.

A preferred example of the compounds of the present invention is the compound having the structural formula IV below:

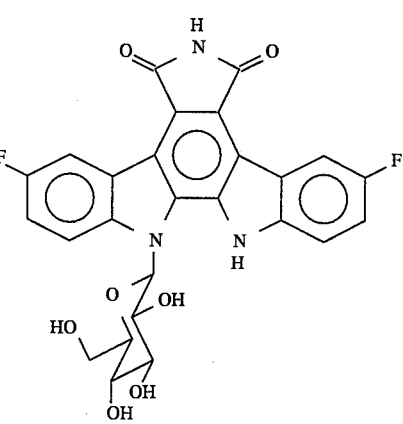

Formula IV

Another preferred example of the compounds of the present invention is the compound having the structural formula V below:

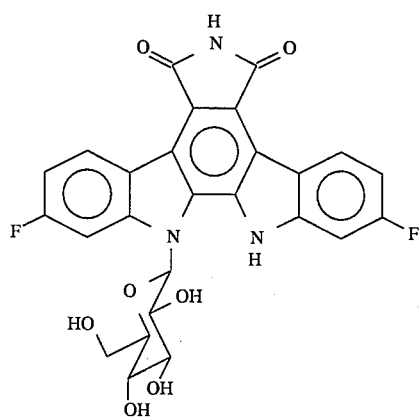

Formula V

Another preferred example of the compounds of the present invention is the compound having the structural formula VI below:

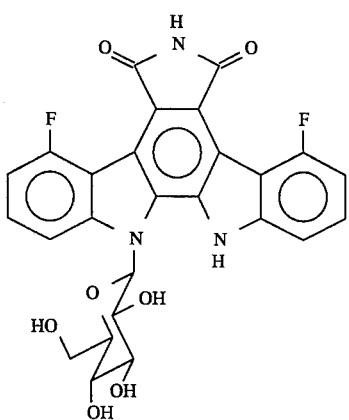

Formula VI

Still another preferred example of the compounds of the present invention is the compound having the structural formula VII below:

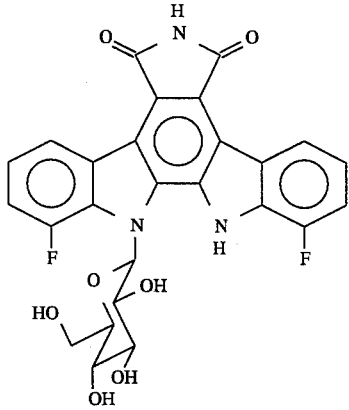

Formula VII

Still another preferred example of the compounds of the present invention is the compound having the structural formula VIII below:

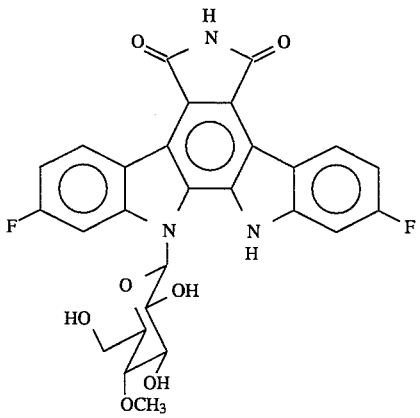

Formula VIII

Another preferred example of the compounds of the present invention is the compound having the structural formula IX below:

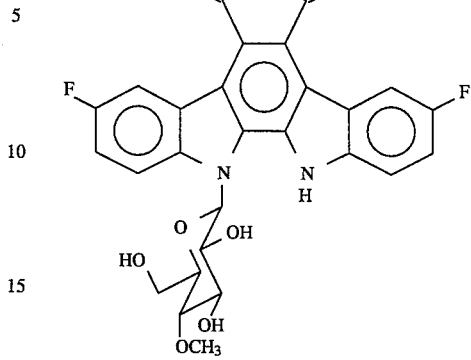

Formula IX

Another preferred example of the compounds of the present invention is the compound having the structural formula X below:

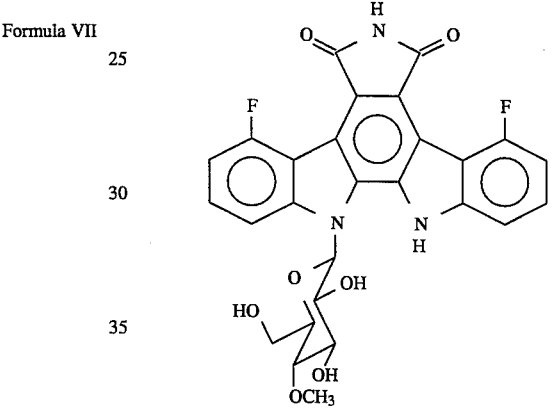

Formula X

Yet another preferred example of the compounds of the present invention is the compound having the structural formula XI below:

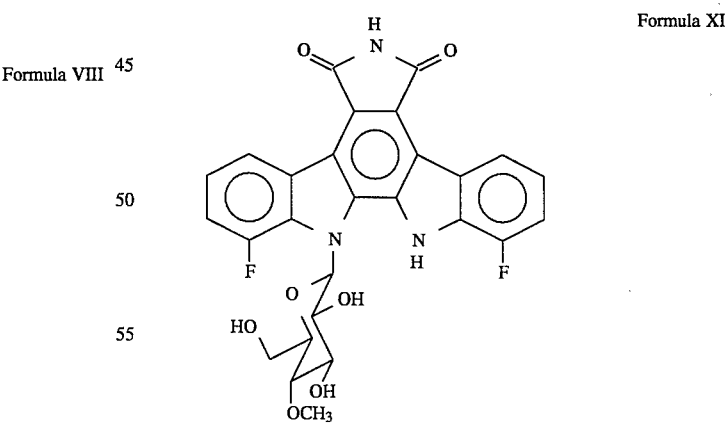

Formula XI

In the present process a tryptophan analog is added to the rebeccamycin fermentation medium and is incorporated during fermentation into the rebeccamycin structure creating a corresponding rebeccamycin analog. A more extensive description of the process is given below and in the illustrative examples which follow.

Preparation of the Antibiotics

The compounds Formulas IV–XI are produced by cultivating a rebeccamycin producing strain of *Saccharothrix aerocglonigenes*, with DL-4-fluorotryptophan, DL-5-fluorotryptophan, DL-6-fluorotryptophan, or DL-7-fluorotryptophan. The preferred producing organism is a novel strain of *Saccharothrix aerocolonigenes*, previously designated as *Nocardia aerocolonigenes* strain C38,383-RK2 (ATCC 39243) in U.S. Pat. No. 4,487,925. Recently, this strain was reclassified as *Saccharothrix aerocolonigenes* (Bush et al., *J. Antibiotics* 40:668–678, 1987) and is designated herein as *Saccharothrix aerocolonigenes* strain C38,383-RK2 (ATCC 39243). This strain was isolated from a soil sample collected in Panama. A biologically pure culture of strain C38,383-RK2 has been deposited with the American Type Culture Collection, Rockville, Md., and added to their permanent collection of microorganisms as ATCC 39243. This culture, designated as C38,383-RK2, is also maintained as a dormant culture in lyophile tubes and cryogenic vials in the Bristol-Myers Squibb Co. Pharmaceutical Research and Development Division Culture Collection, 5 Research Parkway, Wallingford, Conn. 06492.

The taxonomic studies on strain C38,383-RK2 (ATCC 39243) have been described in detail in U.S. Pat. No. 4,487,925 and in *J. Antibiotics* 40:668–678, 1987. The strain has been classified as a novel strain of *Saccharothrix aerocolonigenes*.

It is to be understood that the present invention is not limited to use of the particular preferred strain ATCC 39243 or to organisms fully answering its description. It is especially intended to include other rebeccamycin producing strains or mutants of the described organism which can be produced by conventional means such as x-radiation, ultraviolet radiation, treatment with nitrogen mustard, phage exposure and the like.

In practicing the present process, a rebeccamycin-producing strain of *Saccharothrix aerocolonigenes*, having the identifying characteristics of strain C38,383-RK2 (ATCC 39243), or a mutant or variant thereof, is cultivated in a conventional aqueous nutrient medium supplemented with the appropriate tryptophan analog. For optimal production of the compound of Formulas VI and X, the medium should be supplemented with DL-4-fluorotryptophan. For optimal production of the compounds of Formulas IV and IX, the medium should be supplemented with DL-5-fluorotryptophan. For optimal production of the compounds of Formula V and VIII, the medium should be supplemented with DL-6-fluorotryptophan. For optimal production of the compounds of Formulas VII and XI, the medium should be supplemented with DL-7-fluorotryptophan. The organism is grown in a nutrient medium containing known nutritional sources for actinomycetes. Thus, the organism is grown in a nutrient medium containing an assimilable carbon source such as sucrose, lactose, glucose, rhamnose, fructose, glycerol or soluble starch. The medium should also contain an assimilable nitrogen source such as fishmeal, peptone, peanut meal, cottonseed meal, corn steep liquor, amino acids or ammonium salts. Nutrient inorganic salts can also be incorporated in the medium so as to provide sodium, potassium, ammonium, calcium, phosphate, sulfate, nitrate, carbonate and like ions. Trace elements such as copper, manganese, iron zinc, etc. are added to the medium if desired, or they may be present as impurities of other constituents of the media. Submerged aerobic conditions are preferably employed for the production of large quantities of antibiotic, although for production of limited amounts, surface cultures and bottles may also be used. The general procedures used for the cultivation of other actinomycetes are applicable to the present invention.

Production of the antibiotics of the present invention can be effected by any temperature conducive to satisfactory growth of the producing organism, e.g. 18° to 39° C. and is conveniently carried out at a temperature of about 28° C. The fermentation may be carried out in flasks or in laboratory or industrial fermentors of various capacity.

When tank fermentation is to be used it is desirable to produce a vegetative inoculum in a nutrient broth by inoculating a small volume of the culture medium with a slant, a cryopreservative culture or a lyophilized culture of the producing organism. After obtaining a viable and active inoculum in this manner, it is transferred aseptically to the fermentation tank charged with production medium for large scale production of the antibiotic of the present invention. The medium in which the vegetative inoculum is grown can be the same as, or different from, that utilized in the tank as long as it is such that a good growth of the producing organism is obtained and supplemented with the appropriate fluorotryptophan. Further agitation may be provided by a mechanical impeller. Antifoam agents such as lard oil or silicone oil may also be added if needed. Antibiotic production is monitored by high performance liquid chromatography assay or by conventional biological assay. In general, optimum production of the antibiotics of the present invention is achieved after incubation of about 6 days.

Isolation and purification of the so-obtained derivatives may be carried out by conventional chromatographic procedures.

Physical and Chemical Properties:

The compounds of Formulas IV, V and VIII have the following Physical and Chemical Properties:

Compound of Formula IV

Description: Bright yellow amorphous solid

Molecular Formula: $C_{26}H_{19}F_2N_3O_7$

Molecular weight: 523.454

Mass Spectrum: Kratos MS 25 Mass Spectrometer. FABMS 524 (M+H)$^+$, 361 (M-162, loss of glucose).

Ultraviolet Spectrum: Hewlett Packard 845A Diode Array Spectrophotometer. Concentration 1.0 mg/100 ml MeOH. Neutral $\lambda$max nm (E 1%/1 cm): 405, 322(457), 288, 277, 259, 230(348).

Infrared Spectrum: Perkin-Elmer 1800 FTIR Spectrometer. KBr Pellet (cm$^{-1}$): 3340, 2915, 1752, 1708, 1628, 1591, 1484, 1462, 1392, 1331, 1292, 1247, 1191, 1112, 1081, 1052, 947, 904 795, 762, 752, 752, 511.

360 MHz $^1$H-NMR: Bruker Model AM-3000 Spectrometer. Duel carbon-proton probe, 5 mm. Solvent d$_6$-DMSO. Observed chemical shifts (ppm): 11.76 (s,1H), 11.23(s,1H), 8.85(dd,1H), 8.77(dd,1H), 8.01(dd,1H), 7.68 (dd,1H), 7.46(m,2H), 6.29(d,1H), 6.12(t,1H), 5.45(d,1H), 5.17(d,1H), 4.95(d,1H), 4.07(d,1H), 3.95(m,2H), 3.81(d,1H), 3.59(m,2H).

90 MHz $^{13}$C-NMR: Bruker Model AM-3000 Spectrometer. Proton decoupled spectrum. Duel carbon-proton probe, 5 mm. Solvent d$_6$-DMSO. Observed chemical shifts (ppm): 170.9, 170.8, 157.0(d), 157.0(d), 138.6, 137.2, 130.7, 129.2, 121.7(d), 121.4(d), 121.3, 119.6, 116.6, 115.1, 115.0(d), 114.6(d), 113.3(d), 113.2(d), 109.1(d), 109.1(d), 84.8, 78.7, 76.5, 73.2, 67.6, 58.3.

Solubility: Soluble in DMSO, DMF, THF, acetone, EtOAc, MeOH.

Thin Layer Chromatography (R$_f$ values): Normal phase (silica gel 60); EtOAc: 0.10. EtOAc-MeOH (9:1 v/v): 0.41. Reversed phase (C$_{18}$); 0.1M NH$_4$OAc-MeOH-CH$_3$CN (2:4:4: v/v): 0.67

Compound of Formula V
  Description: Bright yellow amorphous solid
  Molecular Formula: $C_{26}H_{19}F_2N_3O_7$
  Molecular Weight: 523.454
  Mass Spectrum: Kratos MS 25 Mass Spectrometer. FABMS 524 $(M+H)^+$, 361 (M-162, loss of glucose).
  Ultraviolet Spectrum: Hewlett Packard 8452A Diode Array Spectrophotometer. Concentration 1.0 mg/100 ml MeOH. Neutral $\lambda$max nm (E 1%/1 cm): 398(60), 316(640), 280(259), 256(313), 226(526), (497).
  Infrared Spectrum: Perkin-Elmer 1800 FTIR Spectrometer. KBr Pellet ($cm^{-1}$): 3324, 2927, 1745, 1701, 1623, 1580, 1491, 1471, 1452, 1412, 1384, 1330, 1233, 1172, 1116, 1075, 1048, 1016, 963, 916, 829, 764, 745, 646, 635, 617, 498, 490.
  360 MHz $^1$H-NMR: Bruker Model AM-3000 Spectrometer. Duel carbon-proton probe, 5 mm. Solvent $d_6$-DMSO. Observed chemical shifts (ppm): 11.77 (s,1H), 11.18(s,1H), 9.12(dd,1H), 9.05(dd,1H), 7.85(dd,1H), 7.43(dd,1H), 7.23(t, 2H), 6.26(d,1H), 6.24(s,1H), 5.31(d,1H), 5.04(d,1H), 3.98(m,2H), 3.87 (m,1H), 3.66( s,2H).
  90 MHz $^{13}$C-NMR: Bruker Model AM-3000 Spectrometer. Proton decoupled spectrum. Duel carbon-proton probe, 5 mm. Solvent $d_6$-DMSO. Observed chemical shifts (ppm): 170.8, 170.7, 161.8(d), 161.8(d), 143.2(d), 141.5(d), 130.1, 128.7, 126.0(d), 125.9(d), 120.9, 119.3, 118.2, 118.1, 117.7, 116.5, 108.8(d), 108.6(d), 98.9(d), 98.3(d), 84.7, 78.6, 76.5, 73.1, 67.5, 58.3.
  Solubility: Soluble in DMSO, DMF, THF, MeOH, acetone, EtOAc.
  Thin Layer Chromatography ($R_f$ values): Normal phase (silica gel 60); EtoAc: 0.40. EtoAc-MeOH (9:1 v/v): 0.63. Reversed phase ($C_{18}$); 0.1M $NH_4OAc$-MeOH-$CH_3CN$ (2:4:4: v/v): 0.60.

Compound of Formula VIII
  Description: Bright yellow amorphous solid
  Molecular Formula: $C_{27}H_{21}F_2N_3O_7$
  Molecular Weight: 537.481
  Mass Spectrum: Kratos MS 25 Mass Spectrometer. FABMS 538 $(M+H)^+$, 361 (M-176, loss of 4-0-methylglucose).
  Ultraviolet Spectrum: Hewlett Packard 8452A Diode Array Spectrophotometer. Concentration 1.2 mg/100 ml MeOH. Neutral $\lambda$max nm (E 1%/1 cm): 398(103), 316(1050), 280(387), 256(454), 228(780).
  Infrared Spectrum: Perkin-Elmer 1800 FTIR Spectrometer. KBr Pellet ($cm^{-1}$): 3324, 2938, 1747, 1703, 1623, 1580, 1491, 1471, 1452, 1412, 1384, 1330, 1233, 1172, 1140, 1116, 1087, 1054, 963, 918, 828, 764, 649, 635, 618, 498.
  360 MHz $^1$H-NMR: Bruker Model AM-3000 Spectrometer. Duel carbon-proton probe, 5 mm. Solvent $d_6$-DMSO. Observed chemical shifts (ppm): 11.77 (s,1H), 11.18(s,1H), 9.12(dd,1H), 9.05(dd,1H), 7.88(dd,1H), 7.41(dd,1H), 7.23(m,2H), 6.25(d,1H), 6.24(s,1H), 5.36(dd,1H), 5.31(d,1H), 5.04(d,1H), 3.97(m,2H), 3.60–3.95(m,4H).
  90 MHz $^{13}$C-NMR: Bruker Model AM-3000 Spectrometer. Proton decoupled spectrum. Duel carbon-proton probe, 5 mm. Solvent $d_6$-DMSO. Observed chemical shifts (ppm): 170.8, 170.7, 161.8(d), 161.7(d), 143.1(d), 141.5(d), 130.1, 128.7, 126.0(d), 125.9(d), 120.9, 119.4, 118.2, 118.1, 117.7, 116.5, 108.8(d), 108.6(d), 98.7(d), 98.3(d), 84.4, 77.2, 77.2, 76.2, 73.2, 59.9, 58.5 ppm.
  Solubility: Soluble in DMSO, DMF, THF, acetone, EtOAc, MeOH.
  Thin Layer Chromatography ($R_f$ values): Normal phase (silica gel 60); EtoAc: 0.72. EtoAc-MeOH (9:1 v/v): 0.89. Reversed phase ($C_{18}$); 0.1M $NH_4OAc$-MeOH-$CH_3CN$ (2:4:4: v/v): 0.59.

Biological Properties:
Representative compounds of the present invention were tested against the transplanted mouse leukemia P388 to determine in vivo antitumor activity (Tables 1–3). $CDF_1$ mice were implanted intraperitoneally ("ip") with $10^6$ P388 leukemia cells obtained from DBA/2 donor mice bearing this transplantable murine leukemia. The $CDF_1$ leukemic mice were treated ip with either saline (control mice) or doses of the compound of Formulas IV, V and VIII once at Day 1 post-tumor inoculation. These animals were observed daily and their deaths recorded. Average body weight changes (from the day of leukemia implant to the day of last treatment) were determined for all groups as a means of reflecting drug toxicity. The incidence of mice alive in each group on Day 5 post-tumor implant was recorded as an additional means of assessing drug toxicity. No therapeutic result was considered as meaningful if more than 1 mouse per treatment group had died by Day 5. Each treatment group consisted of 4 to 6 mice; control groups contained 10 mice. The number of mice, if any, surviving to Day 30 (the 1st day of the experiment) was also recorded.

Therapeutic efficacy was evaluated by determining the median survival time ("MST") of mice treated with the compound of Formula IV, V and VIII and comparing it to the MST of parallel control mice. This comparison was made by dividing the MST of the former by the latter and multiplying by 100 to derive a parameter called the percent T/C value. A percent T/C of $\geq 125\%$ was considered to represent a meaningful increase in lifespan and, hence, an active result.

As shown in Table 1, the compound of Formula IV is active against P388 leukemia at dose levels ranging from 10 to 90 mg/kg. The best effect was achieved at a dosage of 30 mg/kg and consisted of a percent T/C of 175%. Toxicity was not observed even at the highest dose (90 mg/kg) tested.

As shown in Table 2, the compound of Formula V is active against P388 leukemia at dose levels ranging from 0.8 to 102.4 mg/kg. The best effect was achieved at a dosage of 102.4 mg/kg and consisted of a percent T/C of 178%. Toxicity was not observed even at the highest dose (102.4 mg/kg) tested.

As shown in Table 3, the compound of Formula VIII is active against P388 leukemia at dose levels ranging from 0.8 to 102.4 mg/kg. The best effect was achieved at a dosage of 51.2 mg/kg and consisted of a percent T/C of 206%. Toxicity was not observed at the highest dose (102.4 mg/kg) tested.

TABLE 1

Effect of Compound of Formula IV on P388 Leukemia[a]
(Day 1 Treatment)

| Dose, ip. (mg/kg/inj) | Median Survival Times (Days) | % T/C | Average Weight Change (g) | No. of Mice Alive on Day 5 | No. of Mice Alive on Day 30 |
|---|---|---|---|---|---|
| 90 | 16.5 | 165 | −0.9 | 4/4 | 0/4 |
| 30 | 17.5 | 175 | 0.6 | 4/4 | 0/4 |
| 10 | 14.5 | 145 | 0.7 | 4/4 | 0/4 |
| Control | 10.0 | 100 | | 10/10 | 0/10 |

[a]Mice were implanted with $10^6$ P388 leukemia cells, and treatments with the compound of Formula IV were begun 1 day later. Control mice were given saline injections.

TABLE 2

Effect of Compound of Formula V on P388 Leukemia[a]
(Day 1 Treatment)

| Dose, ip. | Median Survival | % | Average Weight | No. of Mice Alive on | |
|---|---|---|---|---|---|
| (mg/kg/inj) | Times (Days) | T/C | Change (g) | Day 5 | Day 30 |
| 102.4 | 16.0 | 178 | −0.1 | 6/6 | 0/6 |
| 51.2 | 15.0 | 167 | −0.2 | 6/6 | 0/6 |
| 25.6 | 14.5 | 161 | −0.2 | 6/6 | 0/6 |
| 12.8 | 15.0 | 167 | 0.8 | 6/6 | 0/6 |
| 6.4 | 15.0 | 167 | −1.1 | 6/6 | 0/6 |
| 3.2 | 14.0 | 156 | 0.0 | 6/6 | 0/6 |
| 1.6 | 14.0 | 156 | −0.7 | 6/6 | 0/6 |
| 0.8 | 13.0 | 144 | 0.1 | 6/6 | 0/6 |
| Control | 9.0 | 100 | 1.3 | 10/10 | 0/10 |

[a]Mice were implanted with $10^6$ P388 leukemia cells and treatments with the compound of Formula V were begun 1 day later. Control mice were given saline injections.

TABLE 3

Effect of Compound of Formula VIII on P388 Leukemia[a]
(Day 1 Treatment)

| Dose, ip. | Median Survival | % | Average Weight | No. of Mice Alive on | |
|---|---|---|---|---|---|
| (mg/kg/inj) | Times (Days) | T/C | Change (g) | Day 5 | Day 30 |
| 102.4 | 14.5 | 161 | 0.2 | 6/6 | 0/6 |
| 51.2 | 18.5 | 206 | 0.3 | 6/6 | 0/6 |
| 25.6 | 14.0 | 156 | 0.1 | 6/6 | 0/6 |
| 12.8 | 14.5 | 161 | −0.1 | 6/6 | 0/6 |
| 6.4 | 16.0 | 178 | 0.1 | 6/6 | 0/6 |
| 3.2 | 16.5 | 183 | −0.3 | 6/6 | 0/6 |
| 1.6 | 14.0 | 156 | −0.1 | 6/6 | 0/6 |
| 0.8 | 14.0 | 156 | −0.4 | 6/6 | 0/6 |
| Control | 9.0 | 100 | 1.3 | 10/10 | 0/10 |

[a]Mice were implanted with $10^6$ P388 leukemia cells and treatments with the compound of Formula VIII were begun 1 day later. Control mice were given saline injections.

The present invention includes within its scope pharmaceutical compositions which comprise an effective or tumor-inhibiting amount of a rebeccamycin analog of the present invention, or a pharmaceutically acceptable acid addition salt thereof, in combination with an inert pharmaceutically acceptable carrier or diluent.

According to another aspect of the invention, a method is provided for therapeutically treating an animal (preferably mammalian) host effected by a malignant tumor which comprises administering to such host an effective tumor-inhibiting dose of the antibiotic of the present invention or a pharmaceutically acceptable acid addition salt thereof.

Examples of suitable compositions include solid compositions for oral administration such as tablets, capsules, pills, powders and granules, liquid compositions for oral administration such as solutions, suspensions, syrups and elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

It will be appreciated that the actual preferred dosages of the rebeccamycin analogs of the present invention will vary according to the particular compound being used, the particular composition formulated, the mode of application and the particular situs, host and disease being treated. Many factors that modify the action of the drug will be taken into account by those skilled in the art, e.g. age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by those skilled in the art using conventional dosage determination tests.

The present invention is illustrated by the following examples which are not intended to be construed as limiting the scope of the invention.

EXAMPLE 1

Preparation of cryopreservative culture of *Saccharothrix aerocolonigenes* strain C38,383-RK2 (ATCC 39243)

*Saccharothrix aerocolonigenes* strain C38,383-RK2 was maintained as a cryopreservative culture stored at −80° C. in a Revco ultralow temperature freezer. To prepare a cryopreservative culture, strain C38,383-RK2 was transferred in test tubes on slants of yeast-malt extract agar supplemented with $CaCO_3$ which consisted of

| dextrose | 4.0 g |
|---|---|
| yeast extract | 4.0 g |
| malt extract | 10 g |
| $CaCO_3$ | 1.5 g |
| agar | 15 g |
| deionized water q.s. to | 1 liter |

The agar slant was incubated at 28° C. for 7–10 days. Vegetative culture was prepared by transferring the surface growth from the slant culture to a 500 ml Erlenmeyer flask containing 100 ml of a sterile vegetative medium consisting of

| Cerelose (Corn Products) | 30 g |
|---|---|
| Pharmamedia (Traders Oil Mill Co.) | 10 g |
| Nutrisoy (Archer Daniels Midland Co.) | 10 g |
| $CaCO_3$ | 3 g |
| deionized water q.s. to | 1 liter |

This vegetative culture was incubated at 28° C. for 48 hours on a rotary shaker set at 250 rev/min. The vegetative culture was mixed with equal volume of cryoprotective solution consisting of

| Sucrose | 100 g |
|---|---|
| glycerol | 200 g |
| deionized water q.s. to | 1 liter |

Four ml portions of this mixture were transferred to sterile cryogenic tube (5 ml capacity, Corning) and were frozen in a dry ice-acetone bath. The frozen vegetative cultures were then stored at −80° C. in a Revco ultralow temperature freezer.

EXAMPLE 2

Preparation of vegetative culture of *Saccharothrix aerocolonigenes* strain C38,383-RK2 (ATCC 39243)

Vegetative culture was prepared by transferring 4 ml of the cryopreservative culture to a 500 ml Erlenmeyer flask containing 100 ml of a sterile vegetative medium having the same composition as the vegetative medium described in Example 1. The vegetative culture was incubated at 28° C. for 48 hours on a rotary shaker set at 250 rev/min.

EXAMPLE 3

Preparation of the compound of Formula IV

Three ml of the vegetative culture of Example 2 was inoculated into 500 ml Erlenmeyer flasks each containing 100 ml of production medium consisting of

| | |
|---|---|
| Staclipse J-UB starch (A. E. Staley) | 10 g |
| $KH_2PO_4$ | 2 g |
| $MgSO_4$ | 1 g |
| L-threonine | 2.5 g |
| $CaCO_3$ | 2 g |
| deionized water q.s. to | 1 liter |

The production culture was incubated at 28° C. on a rotary shaker set at 250 rev/min. After 48 hours of fermentation, DL-5-fluorotryptophan was added to the culture at a final concentration of 1 mg/ml. The culture was allowed to incubate at 28° C. and shaken at 250 rev/min for additional 4 days. Production of the compound of Formula IV was monitored by HPLC. Optimal production of the compound of Formula IV at a concentration of 23–32 mg/ml was generally obtained at 6 days of fermentation (i.e. 4 days after the addition of DL-5-fluorotryptophan).

EXAMPLE 4

Preparation of the compound of Formula V and VIII.

Three ml of vegetative culture of Example 2 was inoculated into 500 ml Erlenmeyer flasks each containing 100 ml of production medium having the same composition as described in Example 3. The production culture was incubated at 28° C. on a rotary shaker set at 250 rev/min. After 48 hours of fermentation, DL-6-fluorotryptophan was added to the culture at a final concentration of 1 mg/ml. The culture was allowed to incubate at 28° C. and shaken at 250 rev/min for additional 4 days. Production of the compounds of Formula V and VIII were monitored by HPLC. Optimal production of the compound of Formula V and VIII were generally obtained at 6 days of fermentation (i.e. 4 days after the addition of DL-6-fluorotryptophan) at a concentration of 36–58 µg/ml and 31–42 µg/ml respectively.

EXAMPLE 5

Isolation and purification of the compounds of Formulas IV, V and VIII.
a) General Method Solvents were not redistilled before use. Methanol, acetone, ethyl acetate, isopropyl ether, chloroform, tetrahydrofuran, ethyl ether and hexanes were ACS reagent grade. Water for HPLC refers to in-house deionized water from a Barnstead Nanopure II system. Tetrahydrofuran, methanol and acetonitrile for HPLC use were B & J Brand HPLC grade solvents. Ammonium acetate was Fisher HPLC grade.

Normal phase thin layer chromatography (tlc) was carried out on Silica gel 60, F-254 plates (EM Reagents, Cat. #5765, 5×10 cm, by 0.25 mm thick). Reversed phase tlc was accomplished with Whatman $MKC_{18}$ plates (Cat. #4803-110, 0.2 mm thick). Plates were developed in Whatman cylindrical jars with caps and 10 ml of eluant. Rebeccamycin analogs were visible as yellow zones in normal lighting or as yellow fluorescing zones with 254 nm or 366 nm ultraviolet light.

To whole broths was added Dicalite (speed plus) filter aid. After brief stirring the broths were filtered on large Buchner funnels or on a Tolhurst Centerslung Centrifugal Filter Unit (Model 1B15, Ametek, Inc.). Filtrates were discarded. Mycelial mats were stirred in THF or THF-acetone mixtures for one hour, filtered, and the Dicalite further rinsed with acetone until it no longer fluoresced yellow under UV light. The combined filtrates were concentrated under reduced pressure to yield crude extracts.

A vacuum liquid chromatography (VLC) apparatus consists of a Buchner funnel (Kontes, Art. #K-954100) containing a sealed-in sintered glass disc (M porosity), a side hose connection for vacuum and a lower 24/40 joint for attachment of receiving flasks. Initially, the least polar eluting solvents pulled through under vacuum to form tightly packed 5 cm adsorbent bed heights. Samples were preadsorbed onto adsorbent and applied to funnels as slurries, or applied in a solution of the least polar eluting solvent. Step gradients were carried out where predetermined volumes of increasingly polar eluant constituted the fractions. The funnel was sucked dry after each volume of eluant. Fractions were concentrated and combined on the basis of tlc analysis.

Apparatus for size exclusion chromatography consisted of the following: A Glenco column (2.5 I.D.×100 cm) equipped with solvent resistant teflon and plates; Fluid Metering, Inc. FMI lab pump (Model RP-G150); Glenco glass reservoir (500 ml); Isco Model 328 fraction collector. Columns were slurry packed with Sephadex LH-20 (Pharmacia) preswollen in the eluting solvent. Solvent was delivered in a downward manner through the column at a rate controlled by the lab pump.

The following components were used to construct a semi-preparative HPLC system: Waters Associates Model 590 Solvent Delivery System pump; Knauer model 87 Variable Wavelength Detector. Waters Associates model SR-204 Strip Chart Recorder; Whatman Partisil 10 ODS-3 column (10 mm×50 cm); 316 stainless steel tubing (0.23 mm i.d.).
b.) Isolation and purification of the compound of Formula IV Whole broth (5 liters) was filtered with Dicalite and the mycelial mat extracted by stirring in THF (2 liters) for 1 hour. After further filtering, and an additional THF rinse (1 liter), the combined filtrates were concentrated under reduced pressure to yield 4.5 g crude extract. The extract was adsorbed onto 6.5 g Lichroprep Si 60 Silica gel (EM Science, Art. 9336, 15–25 microns) and applied to a 60 ml VLC funnel containing an additional 24.5 g silica gel. A hexane-ethyl acetate step gradient was carried out (200 ml volumes), followed by a 200 ml volume THF wash. The THF wash (156 mg) was dissolved in 4 ml THF and applied to a column containing 160 g Sephadex LH-20 equilibrated with THF (bed height 90 cm, bed volume 430 ml). Flow rate 3.75 ml/min. As could be determined visually, a major yellow band (62 mg) eluted in the first one-fourth of the second bed volume. Final purification was accomplished by reversed phase ($C_{18}$) HPLC chromatography with a flow rate of 4 ml/min (0.1M $NH_4OAc$—THF (60–40)). Detection was at 320 nm. Eluting at 39 minutes was the major analog (23 mg) designated as the compound of the Formula IV.
c.) Isolation and purification of the compounds of Formula V and VIII Whole broth (2 liters) was filtered using Dicalite filter aid. The mycelial mat, after stirring in THF (2 liters) for 45 minutes, was filtered, and rinsed with an additional volume of THF (1.5 liters). The filtrate was concentrated under reduced pressure to yield 3.39 g crude extract. The crude extract was triturated with five 50 ml volumes of THF, which were combined and concentrated to yield 0.74 g of THF soluble residue. This mass contained the bulk of the yellow fluorescing materials. The THF soluble material was adsorbed onto 2 g Silica Gel H (Merck, 10–40 microns) and applied to a 30 ml VLC funnel containing an additional 11 g Silica Gel H. A hexane-ethyl acetate step gradient was carried out using 100 ml volumes of eluant. The two major rebeccamycin analogs were separated cleanly in this manner. The less polar yellow zone (141 mg) eluted with hexane-ethyl acetate (1:1) and the more polar analog (105 mg) with hexane-ethyl acetate (1:3).

The more polar analog (105 mg) was dissolved in 2 ml THF and applied to a column containing 160 g Sephadex LH-20 (bed heigth 90 cm, bed volume 430 ml) preswollen in THF. The flow rate was 4 ml/min. The main yellow band eluted at 1.25 bed volumes as could be determined visually to yield the compound of Formula V (77 mg).

The less polar analog from VLC (141 mg) was dissolved in 2 ml MeOH and applied to a column containing 110 g Sephadex LH-20 preswollen in MeOH (bed heigth 80cm, bed volume 400 ml). The flow rate 3.5 ml/min. The main yellow zone eluted at the end of the fourth bed volume to yield the compound of formula VIII (70 mg).

What is claimed is:

1. A process for producing the rebeccamycin analogs of formula II or III

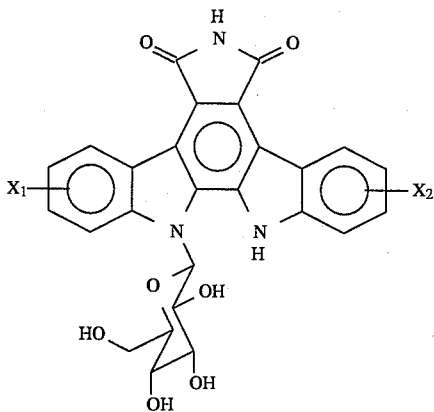

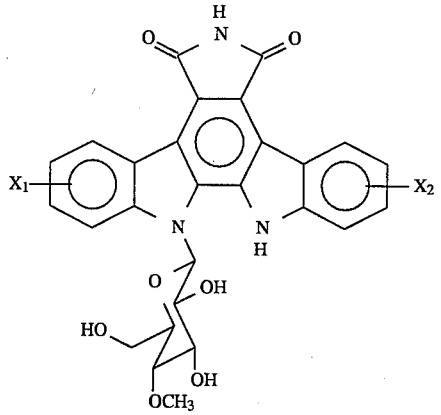

wherein $X_1$ and $X_2$ are independently fluorine or hydrogen, provided that $X_1$ and $X_2$ are not simultaneously hydrogen, or a pharmaceutically acceptable acid addition salt thereof, which comprises cultivating a rebeccamycin-producing strain of *Saccharothrix aerocolonigenes* in an aqueous nutrient medium in the presence of a fluoro-tryptophan analog, until a recoverable amount of the desired rebeccamycin analog is produced by said organism in said culture medium and recovering the desired rebeccamycin analog from the culture medium in a substantially pure form.

2. The process of claim 1 wherein the rebeccamycin-producing strain is *Saccharothrix aerocolonigenes* ATCC 39243.

3. The process of claim 1 wherein the tryptophan analog is DL-4-fluorotryptophan.

4. The process of claim 1 wherein the tryptophan analog is DL-5-fluorotryptophan.

5. The process of claim 1 wherein the tryptophan analog is DL-6-fluorotryptophan.

6. The process of claim 1 wherein the tryptophan analog is DL-7-fluorotryptophan.

* * * * *